US009113996B2

(12) United States Patent
Ramirez

(10) Patent No.: US 9,113,996 B2
(45) Date of Patent: Aug. 25, 2015

(54) HEEL STABILIZATION DEVICE

(71) Applicant: Raymond Ramirez, San Antonio, TX (US)

(72) Inventor: Raymond Ramirez, San Antonio, TX (US)

(*) Notice: Subject to any disclaimer, the term of this patent is extended or adjusted under 35 U.S.C. 154(b) by 357 days.

(21) Appl. No.: 13/733,951

(22) Filed: Jan. 4, 2013

(65) Prior Publication Data

US 2013/0172799 A1 Jul. 4, 2013

Related U.S. Application Data

(60) Provisional application No. 61/582,955, filed on Jan. 4, 2012.

(51) Int. Cl.

| | |
|---|---|
| *A43B 13/14* | (2006.01) |
| *A43B 21/00* | (2006.01) |
| *A43B 21/36* | (2006.01) |
| *A43B 7/14* | (2006.01) |
| *A43B 7/20* | (2006.01) |
| *A43B 7/16* | (2006.01) |
| *A43B 13/00* | (2006.01) |
| *A61F 5/37* | (2006.01) |
| *A61B 19/00* | (2006.01) |
| *A61F 5/00* | (2006.01) |
| *A61F 5/01* | (2006.01) |
| *A43B 13/38* | (2006.01) |
| *A43B 13/37* | (2006.01) |
| *A43B 13/28* | (2006.01) |

(Continued)

(52) U.S. Cl.
CPC . *A61F 5/01* (2013.01); *A43B 13/00* (2013.01); *A43B 13/28* (2013.01); *A43B 13/34* (2013.01); *A43B 13/37* (2013.01); *A43B 13/38* (2013.01); *A43B 13/41* (2013.01); *A43B 21/00* (2013.01); *A43B 21/36* (2013.01); *A61F 5/0111* (2013.01); *A61F 5/0195* (2013.01); *A61F 5/37* (2013.01)

(58) Field of Classification Search
CPC ........ A43B 13/00; A43B 13/28; A43B 13/34; A43B 13/37; A43B 13/38; A43B 13/41; A43B 21/00; A43B 21/36; A61F 5/00; A61F 5/01; A61F 5/0195; A61F 5/37
USPC ....... 36/31, 34 R, 36 A, 88, 89, 92, 103, 105; 128/846, 869, 878; 602/5, 12, 23, 602/27–28
See application file for complete search history.

(56) References Cited

U.S. PATENT DOCUMENTS

| | | |
|---|---|---|
| 4,409,976 A | 10/1983 | Pence |
| 4,817,589 A | 4/1989 | Wertz |

(Continued)

*Primary Examiner* — Alireza Nia
*Assistant Examiner* — Brandon L Jackson
(74) *Attorney, Agent, or Firm* — Buckingham, Doolittle & Burroughs, LLC

(57) ABSTRACT

An adjustable heel stabilization device comprised of first and second side plates, a union plate, a first connector plate for attaching said first side plate with the union plate and a corresponding second connector plate for connecting said second side plate with the union plate, wherein said first and second side plates are repositionable relative to the union plate and vice versa. The adjustable heel stabilization device of the present invention allows an individual to apply pressure to both sides of the heel and compress the skin and tissue along the bottom of the heel together, thereby creating a cushioning effect when the individual is walking, standing or sitting. The adjustable heel stabilization device is adjustable to accommodate various shapes and sizes of footwear, and helps to reduce swelling in the foot and provide relief for heel pain, heel spurs, plantar fasciitis and arch pain.

15 Claims, 5 Drawing Sheets

(51) Int. Cl.
*A43B 13/41* (2006.01)
*A43B 13/34* (2006.01)

(56) References Cited

U.S. PATENT DOCUMENTS

| | | | |
|---|---|---|---|
| 4,982,733 A | 1/1991 | Broadhurst et al. | |
| 5,069,202 A * | 12/1991 | Prock | 602/27 |
| 5,620,413 A | 4/1997 | Olson | |
| 5,678,330 A * | 10/1997 | Van Dyke et al. | 36/89 |
| 6,053,881 A * | 4/2000 | Boodramsingh et al. | 601/70 |
| 6,142,967 A | 11/2000 | Couch | |
| 6,375,633 B1 | 4/2002 | Endress et al. | |
| 6,641,550 B1 | 11/2003 | Johnson | |
| 6,689,081 B2 * | 2/2004 | Bowman | 602/27 |
| 6,991,613 B2 * | 1/2006 | Sensabaugh | 602/27 |
| 7,666,157 B2 * | 2/2010 | Win | 602/23 |
| 8,313,451 B2 * | 11/2012 | Cox | 602/23 |
| 8,657,773 B2 * | 2/2014 | Ostergard | 602/27 |

* cited by examiner

HEEL STABILIZATION DEVICE

CROSS-REFERENCE

This application claims priority from Provisional Patent Application Ser. No. 61/582,955 filed on Jan. 4, 2012.

FIELD OF THE INVENTION

This invention relates to an adjustable heel stabilization device for applying pressure to both sides of the heel to relieve or reduce swelling, and provide support to those suffering from heel pain, heel spurs, plantar fasciitis and arch pain.

BACKGROUND

Anyone who spends prolonged period of time standing on their feet or walking may develop pain in the heels and/or arches of their feet. In fact, it is believed that millions of people around the world periodically experience heel spurs, planter fasciitis or general heel and arch pain in their feet. Sufferers of heel spurs, planter fasciitis or general heel and/or arch pain typically find their mobility limited by such pain and/or discomfort. Further, without a suitable device for supporting the heel, micro tears along the plantar fascia and lateral fascia may not heal properly, worsen inflammation and prolong the discomfort and/or pain that the individual is experiencing.

Without a device for stabilizing the heel, there is no effective way to compress the skin and flesh along the bottom of the heel together to create a cushioning effect for the individual while he or she is standing, walking and/or sitting. Further, without such a stabilization device or the cushioning effect it provides, the heel spur and/or inflamed heel will come into direct contact with the ground and receive the bulk of the impact, resulting in increased discomfort and preventing scar tissue from properly healing.

Consequently, there exists in the art a long-felt need for a heel stabilization device for applying pressure to both sides of the heel to relieve or reduce swelling, and provide support to those suffering from heel pain, heel spurs, plantar fasciitis and arch pain. There also exists in the art a long felt need for a heel stabilization device that compresses the skin and tissue along the bottom of the heel together thereby creating a cushioning effect when the individual is walking or standing. There also exists in the art a long felt need for a heel stabilization device that is adjustable in size to accommodate shoes of various shapes and sizes, and that does not impede the mobility of the wearer. Finally, there is a long-felt need for a an adjustable heel stabilization device that accomplishes all of the forgoing objectives and that is relatively inexpensive to manufacture, aesthetically pleasing, and safe and easy to use.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, is an adjustable heel stabilization device comprised of: a first side plate; a second side plate; a union plate; a first connector plate for moveably attaching said first side plate to said union plate; a second connector plate for moveably attaching said second side plate to said union plate, wherein at least one of said first and second side plates is moveable along a portion of the union plate; and at least one shim pad. In a preferred embodiment of the present invention, both the first and second side plates are independently moveable along at least a portion of the union plate, and said at least one shim pad is repositionable along either first side plate or second side plate. The adjustable heel stabilization device of the present invention may further comprise a strap for removably attaching the device to a wearer's shoe.

The adjustable heel stabilization device of the present invention allows the wearer to apply pressure to both sides of the heel to relieve or reduce swelling, and provide relief for heel pain, heel spurs, plantar fasciitis and arch pain. The adjustable heel stabilization device of the present invention also compresses the skin and tissue along the lower bottom or mid-section of the foot together thereby creating a cushioning effect when the individual is walking, standing or sitting.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

Figure 1:
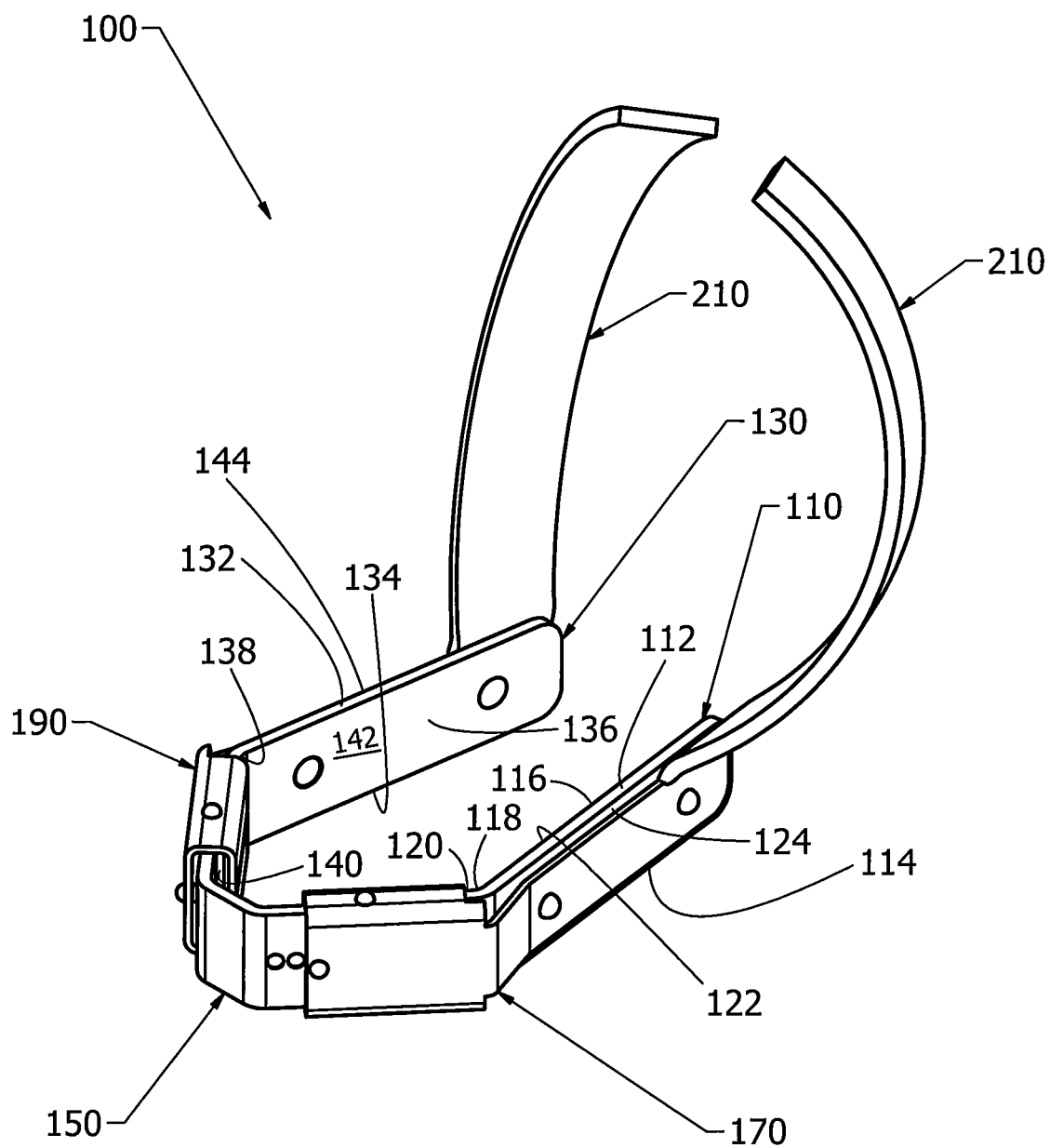
FIG. 1 illustrates a perspective view of a preferred embodiment of the heel stabilization device of the present invention.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details.

The adjustable heel stabilization device of the present invention allows the wearer to apply pressure to both sides of the heel to relieve or reduce swelling, and provide relief for heel pain, heel spurs, plantar fasciitis and arch pain. The adjustable heel stabilization device of the present invention also compresses the skin and tissue along the lower bottom or mid-section of the foot together thereby creating a cushioning effect when the individual is walking, standing or sitting.

Finally, the heel stabilization device of the present invention is relatively inexpensive to manufacture, and safe and easy to use.

Referring initially to the drawings, FIG. 1 illustrates a perspective view of a preferred embodiment of the heel stabilization device 100 of the present invention, which comprises a first side plate 110; a second side plate 130; a union plate 150; a first connector plate 170; a second connector plate 190; and a strap 210. Unless otherwise stated herein, the individual components of device 100 are preferably comprised of a durable metal such as aluminum, though it is contemplated that other suitable materials could also be used, such as plastic, wood, fiberglass, metal, etc., without affecting the overall concept of the invention.

Figure 2:
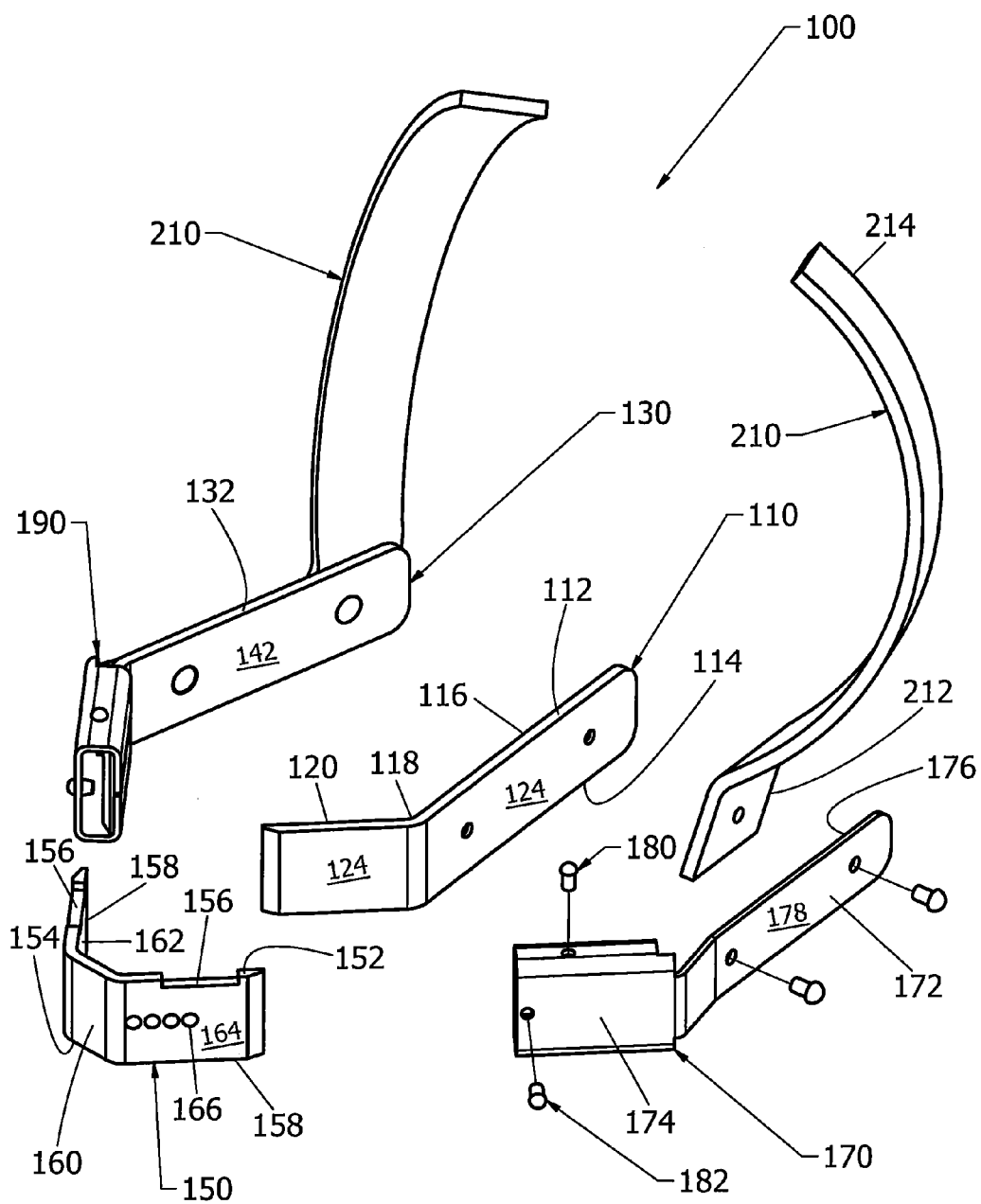
FIG. 2 illustrates a perspective view of a preferred embodiment of the heel stabilization device of the present invention with an exploded view of the various components of one side of the device.

In a preferred embodiment, first side plate 110 is generally rectangular in shape and comprised of a top 112, a bottom 114, a first portion 116, a bend 118, a second portion 120, an inboard surface 122 and an outboard surface 124. First portion 116 is preferably between three and four inches in length as measured from bend 118 to the end of first portion 116, and between ¾ and 1¼ inches in width, as measured from top 112 to bottom 114. Second portion 120 is preferably between 1½ and 2 inches in length as measured from bend 118 to the end of second portion 120, and between ¾ and 1¼ inches in width, as measured from top 112 to bottom 114. As illustrated in FIGS. 1 and 2, bend 118 is formed at the intersection of first portion 116 and second portion 120, and is preferably at an interior angle of between forty-five and fifty five degrees. Inboard surface 122 refers to the surface of first side plate 110 that faces the leg of the wearer, whereas outboard surface 124 refers to the surface of first side plate 110 that faces away from the leg of the wearer. Inboard surface 122 may further comprise a cushion thereon for providing greater comfort to the wearer.

Figure 3:
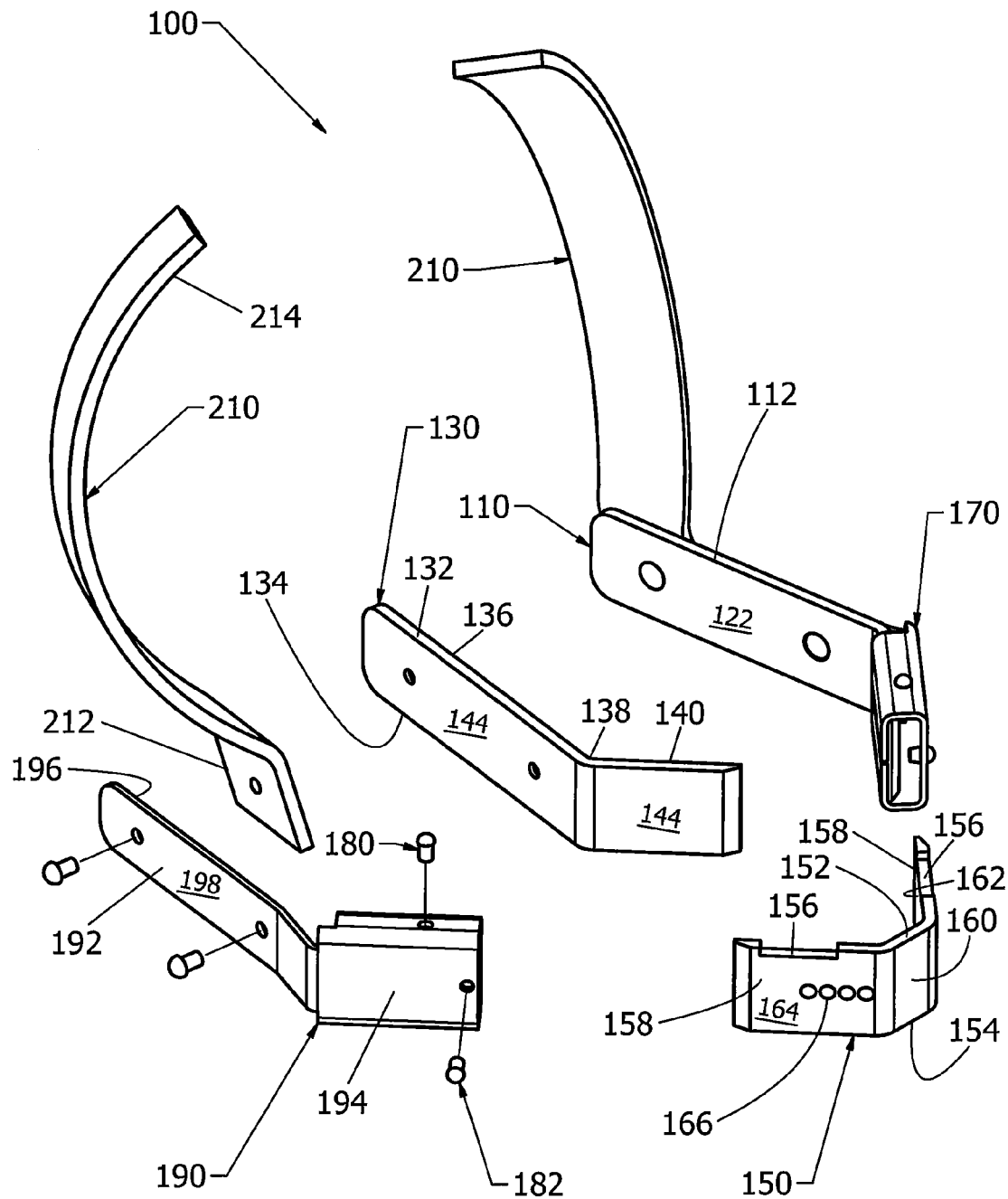
FIG. 3 illustrates a perspective view of a preferred embodiment of the heel stabilization device of the present invention with an exploded view of the various components of the opposite side of the device.

In a preferred embodiment, the shape and size of second side plate 130 should substantially mirror the shape and size of first side plate 110. More specifically, second side plate 130 is generally rectangular in shape and comprised of a top 132, a bottom 134, a first portion 136, a bend 138, a second portion 140, an inboard surface 142 and an outboard surface 144. First portion 136 is preferably between three and four inches in length as measured from bend 138 to the end of first portion 136, and between ¾ and 1¼ inches in width, as measured from top 132 to bottom 134. Second portion 140 is preferably between 1½ and 2 inches in length as measured from bend 138 to the end of second portion 140, and between ¾ and 1¼ inches in width, as measured from top 132 to bottom 134. As illustrated in FIG. 3, bend 138 is formed at the intersection of first portion 136 and second portion 140, which is preferably at an interior angle of between forty-five and fifty-five degrees. Inboard surface 142 refers to the surface of second side plate 130 that faces the leg of the wearer, whereas outboard surface 144 refers to the surface of second side plate 130 that faces away from the leg of the wearer. Inboard surface 142 may further comprise a cushion thereon for providing greater comfort to the wearer.

As illustrated in FIG. 2, union plate 150 is comprised of a top 152, a bottom 154, a slot 156 formed in either the top 152 or bottom 154 for receipt of a pin as described more fully below, two end portions 158 separated by a center portion 160, an inboard surface 162 facing the user's foot and an opposing outboard surface 164. Each of end portions 158 are preferably between 1½ and 2 inches in length as measured from center portion 160 the end of end portion 158, and between ¾ and 1¼ inches in width, as measured from top 152 to bottom 154. Center portion 160 is preferably between ½ and ¾ of an inch in length as measured from one end portion 158 to the other end portion 158, and between ¾ and 1¼ inches in width, as measured from top 152 to bottom 154. Each of end portions 158 preferably extend outwardly from the inboard surface 162 of center portion 160 at an angle of between 45 and 55 degrees. In a preferred embodiment of the present invention, outboard surface 164 of end portions 158 of union plate 150 may further comprise a plurality of indentations or openings 166 for receipt of a second pin, as further described below, and inboard surface 162 may further comprise a cushion thereon for providing greater comfort to the wearer.

As illustrated in FIG. 2, prior to its installation on device 100, first connector plate 170 is generally T-shaped and comprised of a leg portion 172, a body portion 174, an inboard surface 176 and an outboard surface 178. The general size and shape of leg portion 172 preferably conforms to that of first portion 116 of first side plate, and leg portion 172 may be fixedly attached to the outboard surface 124 of first portion 116 by any common means known in the art, such as by welding, rivets, fasteners, glue, etc.

One function of first connector plate 170 is to moveably connect second portion 120 of side plate 110 to one of said end portions 158 of union plate 150 such that the outboard surface 124 of second portion 120 is adjacent to and slidably repositionable along the inboard surface 162 of one of end portions 158, as shown in the FIGS. and described more fully below. In order to moveably connect first side plate 110 to union plate 150, body portion 174 is relatively loosely and substantially wrapped around both second portion 120 of side plate 110 and end portion 158 of union plate 150, as best illustrated in FIG. 1. In this manner, second portion 120 is permitted to slide along the inboard surface 162 of one of end portions 158 to accommodate various shoe sizes and shapes, but is restricted from pulling away from union plate 150 in the inboard direction.

In a preferred embodiment of the present invention, body portion 174 further comprises a first pin 180 that corresponds with slot 156 in union plate 150 and restricts the amount of sliding motion permitted between second portion 120 and end portion 158, and prevents union plate 150 from becoming separated from first side plate 110. The length of slot 156 is preferably between ½ and 1 inch, though other lengths could also be used to suit user preference and permit a greater range of sliding motion between first slide plate 110 and union plate 150 Additionally, body portion 174 may further comprises a second pin 182 that corresponds with said plurality of indentations or openings 166 in the outboard surface 164 of end portions 158 for fixedly attaching first side plate 110 and union plate 150 in a desired position.

Similar to first connector plate 170, second connector plate 190 is also generally T-shaped prior to its installation, and comprised of a leg portion 192, a body portion 194, an inboard surface 196 and an outboard surface 198. The general size and shape of leg portion 192 preferably conforms to that of first portion 136 of second side plate 130, and leg portion 192 may be fixedly attached to the outboard surface 144 of first portion 136 by any common means known in the art, such as by welding, rivets, fasteners, glue, etc.

One function of second connector plate 190 is to moveably connect second portion 140 of second side plate 130 to one of said end portions 158 of union plate 150 such that the outboard surface 144 of second portion 140 is adjacent to and slidably repositionable along the inboard surface 162 of one of end portions 158, as shown in FIG. 3, and described more fully below. In order to moveably connect second side plate 120 to union plate 150, body portion 194 is relatively loosely and substantially wrapped around both second portion 140 of second side plate 130 and end portion 158 of union plate 150, as best illustrated in FIG. 1. In this manner, second portion 140 is permitted to slide along the inboard surface 162 of one of end portions 158 to accommodate various shoe sizes and shapes, but is restricted from pulling away from union plate 150 in the inboard direction.

In a preferred embodiment of the present invention, body portion 194 also further comprises a first pin 180 that corresponds with slot 156 in union plate 150 and restricts the amount of sliding motion permitted between second portion 140 and end portion 158, and prevents union plate 150 from becoming separated from second side plate 130. The length of slot 156 is preferably between ½ and 1 inch, although other lengths could also be used to suit user preference and permit a greater range of sliding motion between second slide plate 130 and union plate 150 Additionally, and in the same fashion described above relative to first connector plate 170, body portion 194 may further comprises a second pin 182 that corresponds with said plurality of indentations or openings 166 in the outboard surface 164 of one of end portions 158 for fixedly attaching the second side plate 130 and union plate 150 in a desired position.

Figure 5:
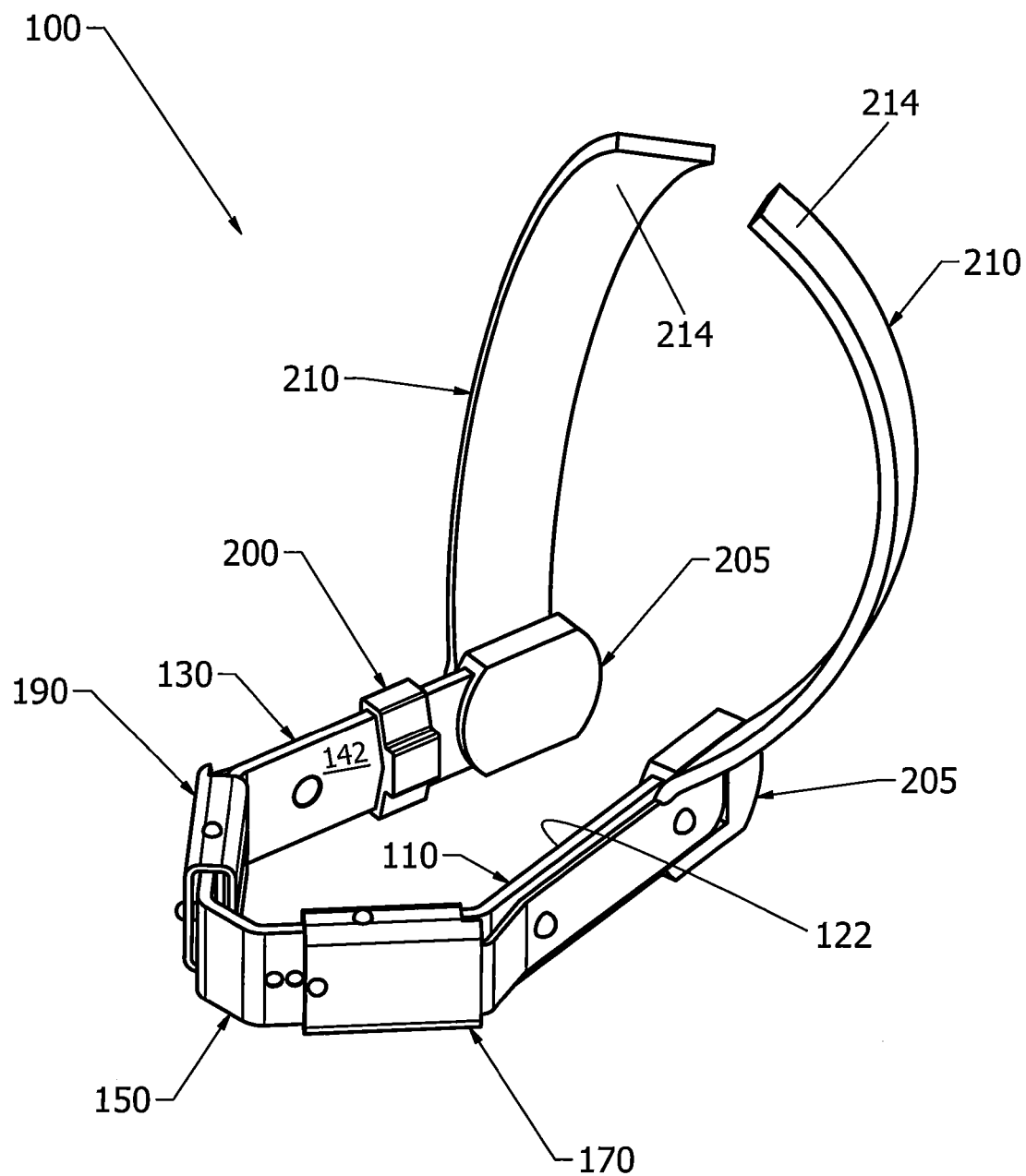
FIG. 5 illustrates a perspective view of the heel stabilization device of the present invention further comprised of a shim pad.

In a preferred embodiment of the present invention, device 100 may further comprise shim pads 200 that can be positioned and repositioned along one or more of the inboard surfaces 122, 142 of said first side plate 110 and/or said second side plate 130, respectively, as shown in FIG. 5. Shim pads 200 apply added lateral pressure to the sides of a wearer's heel, arch area and both sides of a user's foot, and are useful for applying concentrated pressure to a particular position along the wearer's foot. Shim pads 200 are preferably comprised of plastic, metal, wood, fiberglass or any other suitable materials and may be generally C-shaped and sized to accommodate the shape of side plates 110, 130 and slide therealong. Notwithstanding, it is also contemplated that cushions could also be fixedly attached to a desired location of the inboard surfaces 122, 142 of side plates 110, 130, respectively.

Additionally, device 100 may further comprise an extension pad 205 that can be positioned and repositioned along one or more of the ends of said first side plate 110 and/or said second side plate 130, respectively, as shown in FIG. 5. Extension pads 205 enable a wearer to extend the overall length of first and/or second side plates 110, 130 in a direction opposite that of union plate 150, and apply lateral pressure to the sides of the wearer's foot. Extension pads 205 are preferably comprised of plastic, metal, wood, fiberglass or any other suitable materials and further comprise an opening therein for receipt of the end of one of side plates 110, 130. To lengthen said first or second side plates 110, 130, the wearer will simply slide or reposition extension plate 150 along first and/or second side plates 110, 130 in a direction opposite that of union plate 150, thereby enabling the wearer to apply lateral pressure to the sides of the wearer's foot closer to the toes. In a preferred embodiment of the present invention, extension pads 205 will enable the wearer to increase the overall length of one or more of side plates 110, 130 by between ¼ and 1 inch.

As previously mentioned, heel stabilization device also preferably comprises a strap or straps 210 for removably attaching device 100 to a wearer's shoe 220, as shown in the FIGS. Each of said straps 210 preferably comprises a first end 212 and a second end 214, and may be comprised of neoprene, or any other suitable material. First end can be attached to first side plate 110 by any common means known in the art. For example, first end 212 may be fixedly attached by sandwiching the same between first side plate 110 and first connector plate 170, as shown in FIGS. 1 and 2. A first end 212 of a second strap 210 can be attached to second side plate 130 in a similar fashion. Further, the second ends 214 of first and second straps 210 can be removably attached to one another by any common means known in the art once device 100 is installed on shoe 220 in the desired location. For example, said second ends 214 can be joined together by tying, hook and loop fasteners, claps, buttons, or any other suitable means known in the art without affecting the overall concept of the present invention. Nonetheless, it is also contemplated that a single strap can be used to connect first side plate 110 and second side plate 130, and removably attached device 100 to shoe 220.

It is also contemplated that the various inboard surfaces described herein can be lined with a cloth, fabric, cushion, or other suitable materials to provide comfort to the wearer and reduce the likelihood that device 100 will cause damage or scuffing to the exterior surface of shoe 220.

Figure 4:
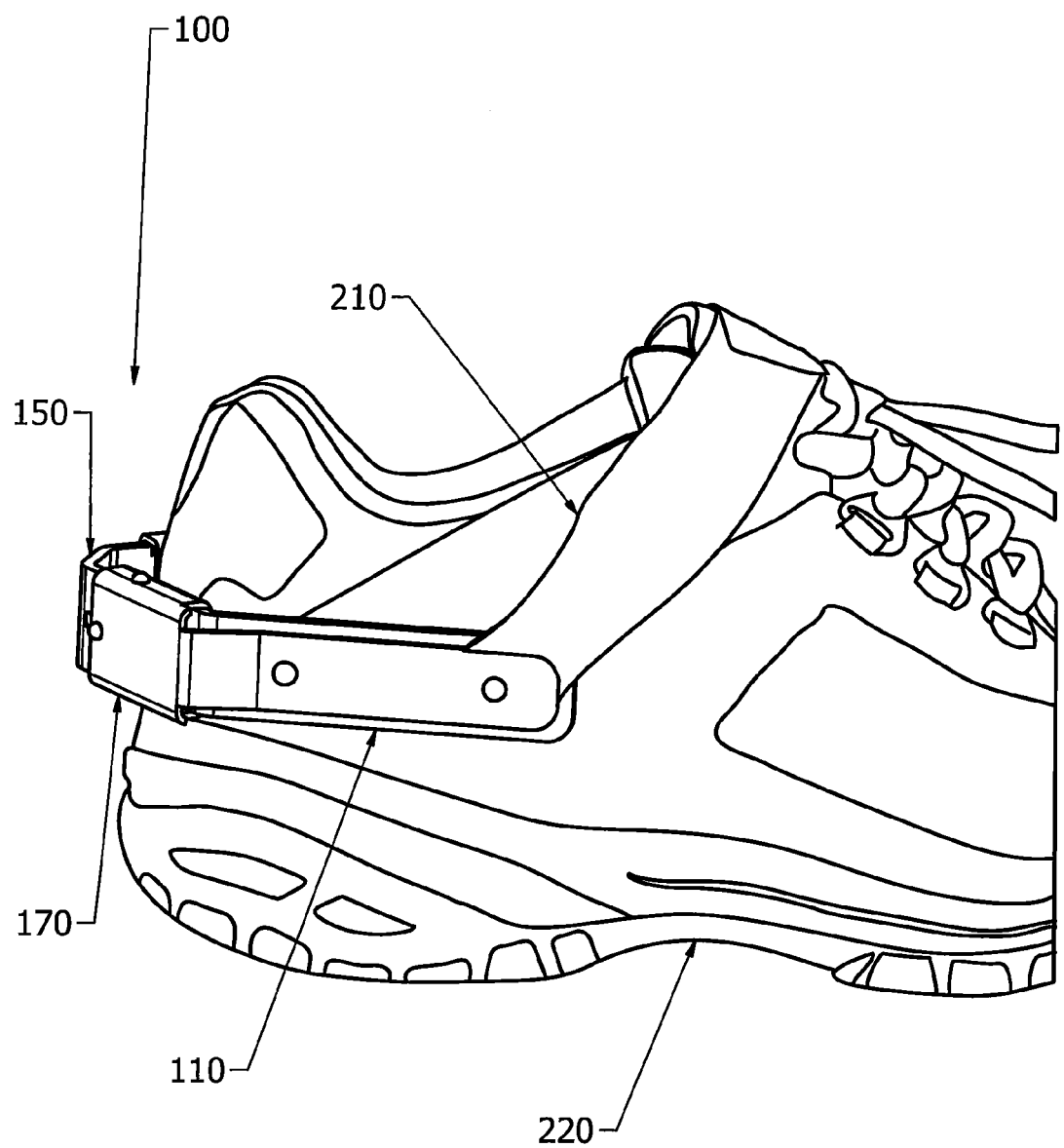
FIG. 4 illustrates a perspective view of a preferred embodiment of the heel stabilization device of the present invention installed on a wearer's shoe.

Having now described the preferred embodiment of the heel stabilization device of the present invention, its use and usefulness will now be described. A user desiring to utilize device 100 would simply install device 100 on his or her shoe 220, as shown in FIG. 4, and secure the device 100 to the show via strap 210. Because first and second side plates 110, 130 are moveably connected to union plate 150, device 100 is capable of accommodating various shapes and sizes of shoes. Once installed, device 100 applies lateral compression from the rear heel area of the wearer to both sides of the wearer's heel, to the arch area and to the outer lateral side of the wearer's foot (not shown) via first and second side plates 110, 130, as well as via optional shim pads 200 that may be installed on and repositioned along one or both of first side plate 110 and/or second side plate 130, as previously described. The optional shim pads 200 allow a wearer to pinpoint where along the foot the lateral compression forces from device 100 should be applied.

By compressing the bottom portion of the wearer's foot, the outer skin and inner muscle tissue located on the bottom of the wearer's heel and arch area will also compress together thereby providing a cushioning affect. It is believed that the combination of the lateral foot compression, the outer skin and muscle tissue compression and the cushioning affect will absorb and distribute the forces applied to the wearer's foot while walking, running, exercising, etc.

It is further believed that use of device 100 causes the heel bone to lift slightly, which in turn helps to alleviate pain caused by a heel spur and allow the healing process to begin. More specifically, it is believed that the internal tissue being damaged by the heel spur will begin to heal and develop scar tissue after approximately four to 10 weeks. Once the affected area has sufficiently healed, it is believed that the scar tissue will become more resistant to possible damage from a heel spur, and the device 100 will no longer need to be worn.

Device 100 eases the pain associated with planter fasciitis and allows the micro tears along the ligaments to heal properly. Device 100 also provides a massage like sensation to the sides of the foot, heel area and arch of the foot with every step taken by the wearer as the impact of each step tends to expand the outer skin and muscle tissue located at the bottom of the wearer's heel and arch area. Further, device 100 produces a counter force against both lateral walls of the shoe and the lateral walls of the heel and arch.

Consequently, the adjustable heel stabilization device of the present invention allows an individual to apply pressure to both sides of the heel and compress the skin and tissue along the bottom of the heel together, thereby creating a cushioning effect when the individual is walking, standing or sitting. The device does not impede mobility or interfere with the daily activities of the wearer, and can be worn while resting, walking, jogging and/or hiking. The adjustable heel stabilization device helps to reduce swelling in the foot and provide relief for heel pain, heel spurs, plantar fasciitis and arch pain. The device can also be worn while the individual is sleeping to reduce swelling.

Additionally, the heel stabilization device is adjustable in size to accommodate a shoeless foot or a foot within a shoe, and allows for adjustable levels of pressure to be applied. Prolonged use of the device is believed to facilitate the healing of scar tissue and minor tears in the plantar fasciitis nerves. Anyone who suffers from heel pain, heel spurs, plantar fasciitis and arch pains would benefit from the physical comfort the heel stabilization device provides. Finally, the heel stabilization device of the present invention is relatively inexpensive to manufacture, and safe and easy to use.

Moreover, other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A heel stabilization device comprising:
   a first side plate;
   a second side plate;
   a union plate, wherein the union plate comprises a plurality of openings therein to limit the movement of one or more of said first side plate and said second side plate;
   a first connector plate for attaching said first side plate to said union plate; and
   a second connector plate for attaching said second side plate to said union plate, wherein at least one of said first and second side plates is moveable along a portion of the union plate.

2. The heel stabilization device of claim 1 further comprising a means for limiting the movement of at least one of said first and second side plates relative to the union plate.

3. The heel stabilization device of claim 2 wherein said means is comprised of a pin and an opening for receipt of said pin.

4. The heel stabilization device of claim 1 further comprising a shim pad repositionable along at least one of said first side plate or said second side plate.

5. The heel stabilization device of claim 1 further comprising a strap for attaching the heel stabilization device to a user's foot.

6. The heel stabilization device of claim 1 wherein both the first side plate and the second side plate are independently moveable along a portion of the union plate.

7. A heel stabilization device comprising:
   a first side plate;
   a second side plate;
   a union plate, wherein the union plate comprises a plurality of openings therein to limit the movement of one or more of said first side plate and said second side plate;
   a first connector plate;
   a second connector plate;
   a shim pad; and
   a strap for attaching said heel stabilization device to a wearer's shoe.

8. The heel stabilization device of claim 7 wherein at least one of said first side plate and said second side plate is moveable relative to said union plate.

9. The heel stabilization device of claim 7 wherein both of the first side plate and the second side plate are moveable relative to said union plate.

10. The heel stabilization device of claim 7 wherein at least one of said first connector plate and said second connector plate comprises a pin for limiting the movement of one or more of said first and second side plates relative to the union plate.

11. The heel stabilization device of claim 7 wherein at least one of the first side plate, the second side plate and the union plate is further comprised of an inboard surface with a cushion located thereon.

12. A heel stabilization device comprising:
   a first side plate;
   a second side plate, wherein an extension pad is attached to at least one of said first and second side plates;
   a union plate;
   a first connector plate for attaching said first side plate to said union plate;
   a second connector plate for attaching said second side plate to said union plate, wherein at least one of said first and second side plates is moveable along a portion of the union plate;
   at least one shim pad;

a strap for attaching said heel stabilization device to a wearer's shoe; and a means for limiting the movement of at least one of said first and second side plates relative to the union plate, wherein said means is comprised of a pin and an opening on the union plate for receipt of said pin.

13. The heel stabilization device of claim 12 wherein said pin is located on at least one of said first and second connector plates.

14. The heel stabilization device of claim 12 wherein said at least one shim paid is repositionably attached to at least one of said first and second side plates.

15. The heel stabilization device of claim 12 wherein at least one of the first side plate, the second side plate and the union plate is further comprised of an inboard surface with a cushion located thereon.

\* \* \* \* \*